(12) United States Patent
Biava et al.

(10) Patent No.: US 8,012,970 B2
(45) Date of Patent: Sep. 6, 2011

(54) DERIVATIVES OF 1-{[1,5-BIS(4-CHLOROPHENYL)-2-METHYL-1H-PYRROL-3-YL]METHYL}-4-METHYLPIPERAZINE, SYNTHESIS PROCESS AND USES THEREOF

(75) Inventors: Mariangela Biava, Rome (IT); Fabrizio Manetti, Castelnuovo Berardenga (IT); Delia Deidda, Siena (IT); Raffaello Pompei, Cagliari (IT); Maurizio Botta, Castelnuovo Berardenga (IT); Giulio Cesare Porretta, Rome (IT)

(73) Assignee: Universta' Degli Studi di Siena, Siena (IT)

( * ) Notice: Subject to any disclaimer, the term of this patent is extended or adjusted under 35 U.S.C. 154(b) by 0 days.

(21) Appl. No.: 13/033,117

(22) Filed: Feb. 23, 2011

(65) Prior Publication Data
US 2011/0144109 A1    Jun. 16, 2011

Related U.S. Application Data

(63) Continuation of application No. 11/817,678, filed on Jun. 24, 2009, now Pat. No. 7,910,581, which is a continuation-in-part of application No. PCT/IT2006/000131, filed on Mar. 3, 2006.

(30) Foreign Application Priority Data

Mar. 4, 2005  (IT) ................. RM05A0094

(51) Int. Cl.
*A61K 31/5377*  (2006.01)
*C07D 413/06*  (2006.01)

(52) U.S. Cl. ..................... 514/235.5; 544/141
(58) Field of Classification Search ............... 514/235.5; 544/141
See application file for complete search history.

(56) References Cited

U.S. PATENT DOCUMENTS
6,610,723 B2   8/2003  Alanine et al.

FOREIGN PATENT DOCUMENTS
DE    3819037 A1   12/1989
JP    62-178590    8/1987

OTHER PUBLICATIONS

Patani et al., "Bioisosterism: A Rational Approach in Drug Desing" 1996, Chem. Rev., 96, 3147-3176.
Biava et al., "Antimycobacterial compounds. Optimization of the BM 212 structure, the lead compound . . . " Bioorganic & Medicinal Chemistry, vol. 13, pp. 1221-1230 (2005).
Wermuth "Molecular variations based on isoteric replacements" The Practice of Medicinal Chemistry, pp. 203-237 (1996).

*Primary Examiner* — Golam M M Shameem
*Assistant Examiner* — Kristin Bianchi
(74) *Attorney, Agent, or Firm* — Lucas & Mercanti, LLP

(57) ABSTRACT

The present invention concerns pyrrole compounds, derivatives of 1-{[1,5-bis(4-chlorophenyl)-2-methyl-1H-pyrrol-3-yl]methyl}-4-methylpiperazine (BM212). The invention concerns the use of the described compounds as antitubercular agents having high activity and low toxicity and process to obtain intermediates and final compounds.

22 Claims, No Drawings

DERIVATIVES OF 1-{[1,5-BIS(4-CHLOROPHENYL)-2-METHYL-1H-PYRROL-3-YL]METHYL}-4-METHYLPIPERAZINE, SYNTHESIS PROCESS AND USES THEREOF

This application is a continuation of U.S. application Ser. No. 11/817,678 filed on Jun. 24, 2009, which is a U.S. national stage of PCT/IT06/00131 filed on Mar. 3, 2006, which claims priority to and the benefit of Italian Application RM2005A000094 filed on Mar. 4, 2005, the contents of which are incorporated herein by reference in their entirety.

FIELD OF THE INVENTION

The present invention concerns novel pyrrole compounds, derivatives of 1-{[1,5-bis(4-chlorophenyl)-2-methyl-1H-pyrrol-3-yl]methyl}-4-methylpiperazine (BM212). The invention concerns the use of the described compounds as antitubercular agents and a process to obtain intermediates and final compounds. The compounds of the invention are found to be more active and much less toxic than previously known compounds.

STATE OF THE ART

Tuberculosis (TB) is an infectious disease caused by *Mycobacterium tuberculosis* (MTB) responsible for a high death-rate in both industrialized and developing countries. According to a recent report compiled by the World Health Organization (WHO), the total number of new cases of TB in 2004 has risen to 9 million worldwide (Duncan et al. 2004). This is particularly alarming considering that these cases represent only 32% of the actual incidence.

The recent recrudescence of TB, due in particular to the increased incidence of the *M. avium* complex (MAC) infection in HIV-infected individuals, has prompted a vigorous search for new drugs for the treatment of the disease. In fact, the progressive immunological deterioration associated with AIDS is often accompanied by opportunistic infections causing TB (*M. tuberculosis*), a non-TB (*M. avium*) mycobacterial disease and mycotic infections caused by *Candida albicans* and *Cryptococcus neoformans*. Treatment of these infections, along with other opportunistic infections which cause the majority of all AIDS-related deaths, is often complicated by patient intolerance to the drugs employed or pathogen resistance to conventional drug therapy.

Drugs currently used to treat TB are Isoniazid (INH), Rifampicin (RIF), Pyrazinamide (PZA), Ethambutol (EMB), Streptomycin (SM), Cycloserin, para-aminosalicylic acid (PAS). Moreover, for most of them, the mechanism of action is known. Indeed, INH and EMB inhibit mycolic acid biosynthesis, a fundamental component of the mycobacterial cell wall, acting at different steps of its synthesis. RIF inhibits the mRNA synthesis by binding to the β subunits of the DNA-dependent bacterial RNA polymerase. SM inhibits bacterial protein synthesis by interfering with molecular structures of the ribosomal 30S subunit. Cycloserin inhibits alanine racemase, which converts L-alanine to D-alanine, thus preventing its incorporation into the pentapeptide peptidoglycan of the bacterial cell wall. Finally, PAS is an antagonist of folates synthesis.

Recent studies demonstrated that nearly 19% of TB isolates in a hospital were resistant to INH and RIF, the two most common antitubercular agents. In general, resistance to INH and SM is more common than resistance to RIF, EMB and PZA.

For an empiric treatment of all MTB infections, even if drug resistance is not suspected, the four-drug regimen of INH, RIF, PZA, and EMB (or SM) until susceptibility results, becomes available. Duration of therapy should be at least one year. However, very often this kind of therapy causes patient intolerance. For this reason, the search for new drugs is deemed necessary and the strategy followed has been to test known antibacterial drugs as antimycobacterial compounds. As a consequence, fluoroquinolones, oxazolidinones, β-lactams and macrolides are the newer drugs introduced in the therapy of antimycobacterial infections. Unfortunately, though these drugs revealed to be active, all of them rapidly develop resistance upon a prolonged treatment. Thus, they must always be used in conjunction with at least another antitubercular drug to which mycobacteria are susceptible.

Fluoroquinolones demonstrated in vitro and in vivo activity against MTB and they are also able to penetrate human macrophages in which mycobacteria live in their latent state. As an example, Levofloxacin is characterized by very favorable pharmacokinetic properties. However, new fluoroquinolones have been studied such as Sitafloxacin, Gatifloxacin and Moxifloxacin, all of them being more active than those already employed in therapy. In any case, quinolones are useful in association with other drugs because they can induce resistance.

Moreover, many efforts have been made to broaden the activity of oxazolidinones (i.e., antibacterial effects) to mycobacteria.

Among β-Lactams, Amoxicillin-Clavulanate (amoxicillin-clavulanic acid association) is used as additive therapy for multidrug resistant (MDR)-TB, demonstrating a favorable patient response.

Macrolides as Claritromycin, Azithromycin and, more recently, Rifapentine revealed less active in vitro against MTB than fluoroquinolones. In general, they are used in combination with at least another drug in order to prevent resistance.

In this context, the search for new effective compounds endowed with a different mode of action seemed a possible solution to the above-mentioned intolerance and drug-resistance problems. Moreover, since in immunocompromised patients, tubercular pathology is very often accompanied by mycotic infections caused by *Candida albicans, Candida* sp. and *Cryptococcus neoformans*, this concomitance has suggested to search for new substances able to act both as antifungal and antimycobacterial.

The authors of the present invention have already synthesized antitubercular compounds with general structure 1 (Deidda et al., 1998, Biava et al., 1999, Biava et al., 1999b)₁

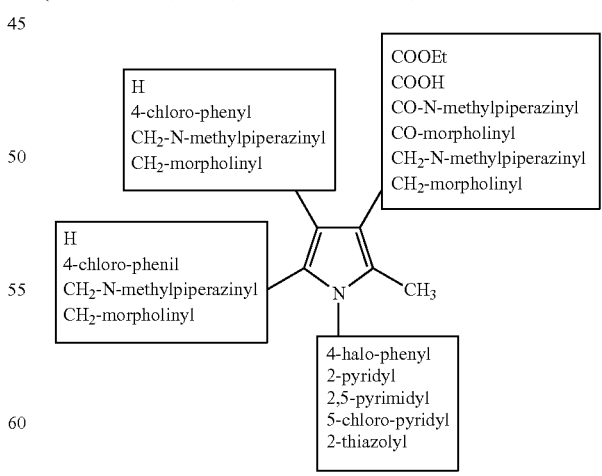

In particular, among them, the compound having the formula shown below, BM212, was identified as the most active, showing a potent and selective antifungal and antimycobacterial activity (Biava et al., 2003).

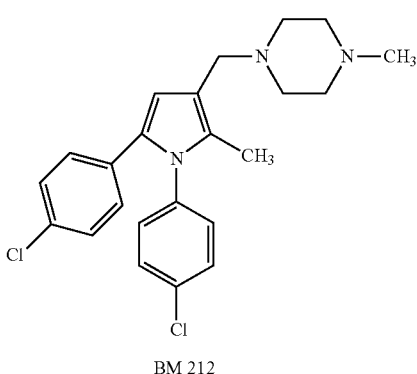

BM 212

More recently, other compounds have been synthesized by the authors, having the general structure 2 (Biava et al., 2004, Biava et al., 2005).

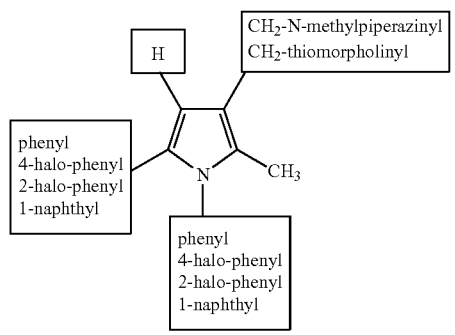

These compounds showed an antitubercular activity against both MTB and other atypical mycobacteria.

Patent application WO04/026828 describes pyrrole derivatives having antimycobacterial activity against clinically relevant strains of MTB. The compounds are assayed in vitro on MTB 27294 and on sensitive and resistant clinical isolates of this species. However, patent application WO04/026828 does not report data concerning maximum 50% non-toxic dose ($MNTD_{50}$), neither the protection index of compounds derived from N-methylpiperazine. It is important to note that the in vitro activity (MIC), the cytotoxicity (MNTD) and, consequently, the protection index (PI) of a compound should be all reported and evaluated at the same time to affirm that such a compound could be an efficient antitubercular agent. In fact, very low MIC values (i.e., high inhibitory properties) associated with high cytotoxicity lead a compound to be discarded. On the contrary, slightly higher MIC values (i.e., lower inhibitory properties) associated with no cytotoxicity (high values of MNTD) are optimal properties that a compounds should have to be classified as a putative antitubercular agent. Moreover, on the basis of the author's previous work, it is also important to note that, in general, compounds with a N-methylpiperazine moiety inserted in a pyrrole scaffold usually showed higher toxicity, with respect for example to the thiomorpholino moiety, even if MIC values of N-methylpiperazine derivatives were better than the corresponding thiomorpholino analogues.

The instant invention refers to compounds that are partially comprised in the general formula of WO04/026828. However, they are not there exemplified nor their activity is demonstrated or even suggested.

The authors of the invention assayed active compounds on different species of mycobacteria, including species that are responsible of tubercular diseases in HIV positive patients, namely M. avium. As a matter of fact, WO04/026828 is silent on the activity on extracellular M. avium. As to the activity of compounds on intracellular M. avium, WO04/026828 reports some activity.

Moreover, the authors of the instant invention are able to present data on $MNTD_{50}$ and protection index, which allow to determine the effectiveness of the compounds as antitubercular agents. In fact, only upon the achievement of all of data (inhibitory activity and cytotoxicity) it is possible to select compounds that are effectively usable as antimycobacteria, including relevant species of atypical mycobacteria such as M. avium. Best compounds are characterized by both a high activity and a low cytotoxicity.

In addition, the compounds of the present invention display a high activity against intramacrophagic M. tuberculosis. These results indicate that such compounds are active in an early stage of the disease, where latent tuberculosis occurs before the development of active tuberculosis. Therefore the inactivation of mycobacteria in latent phase is crucial to reduce the percentage of progression towards active tuberculosis. Such percentage is particularly high in immuno-compromised patients, for instance HIV positive subjects. WO04/026828 does not report any activity on intramacrophagic M. tuberculosis.

SUMMARY OF THE INVENTION

The invention aims at providing antimycobacterial compounds endowed with a high activity toward Mycobacteria and a low cytotoxicity, i.e. with a very good Protection Index (PI, defined as the ratio between cytotoxic concentration and inhibitory concentration). This is particularly important in view of the fact that antimycobacterial drugs are very often administered to immunocompromised patients for whom drug toxicity is the effective cause of death. The described derivatives possess excellent antimycobacterial activity, and they are 1. more active than existing drugs
2. less toxic than existing drugs
3. very active against dormient mycobacteria
4. very active against resistant mycobacteria It is therefore an object of the present invention a compound having the general formula I or II,

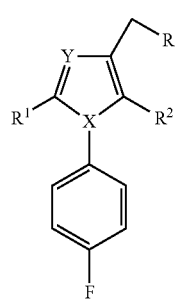

I

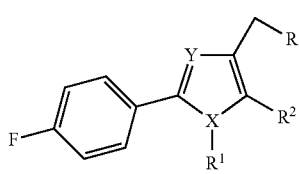

in which:

R represents a morpholinyl, thiomorpholinyl, N-methylpiperazinyl, N-isopropylpiperazinyl, N-acetylpiperazinyl, piperidyl or imidazolyl group;

$R^1$ is either absent or represents a hydrogen or an o-methylphenyl, m-methylphenyl, p-methylphenyl, o-ethylphenyl, m-ethylphenyl, p-ethylphenyl, o-propylphenyl, m-propylphenyl, p-propylphenyl, o-isopropylphenyl, m-isopropylphenyl, p-isopropylphenyl, o-methoxyphenyl, m-methoxyphenyl, p-methoxyphenyl, o-trifluoromethylphenyl, m-trifluoromethylphenyl, p-trifluoromethylphenyl, o-chlorophenyl, m-chlorophenyl, p-chlorophenyl, o,o-dichlorophenyl, m,m-dichlorophenyl, o,p-dichlorophenyl, o-fluorophenyl, m-fluorophenyl, p-fluorophenyl, o,o-difluorophenyl, m,m-difluorophenyl, o,p-difluorophenyl, 1-naphthyl;

$R^2$ is H, methyl, ethyl, isopropyl, benzyl, o-chlorobenzyl, m-chlorobenzyl, p-chlorobenzyl, o-fluorobenzyl, m-fluorobenzyl, p-fluorobenzyl, o-methylbenzyl, m-methylbenzyl, p-methylbenzyl, o-trifluorobenzyl, m-trifluorobenzyl, p-trifluorobenzyl, o-methoxybenzyl, m-methoxybenzyl, p-methoxybenzyl;

wherein if the compound has the general formula I, X=N and Y=N or CH;

wherein if the compound has the general formula II, X=O, S or N and Y=N or CH (for compounds with general formula II, wherein X=O or S, $R^1$ cannot exist);

wherein compound with the general formula I, in which X=N, Y=CH, R=N-methylpiperazinyl or thiomorpholinyl, $R^1$=p-chlorophenyl or p-fluorophenyl and $R^2$=CH$_3$ is not included in the present invention;

wherein compound with the general formula II, in which X=N, Y=CH, R=N-methylpiperazinyl or thiomorpholinyl, $R^1$=p-chlorophenyl or p-fluorophenyl and $R^2$=CH$_3$ is not included in the present invention;

wherein compound with the general formula II, wherein X=O, Y=CH, R=imidazolyl, $R^1$ is not present and $R^2$=CH$_3$ is not included in the present invention.

In a preferred embodiment form, the compound has the general formula I, in which X=N; Y=CH; R=thiomorpholinyl or N-methylpiperazinyl; $R^2$=methyl; $R^1$=o-chlorophenyl, o-fluorophenyl, p-methylphenyl, o,p-dichlorophenyl, o,p-difluorophenyl, 1-naphthyl. Preferably, compounds bear the residues R e $R^1$ shown in Table 1.

TABLE 1

| Compd | R | $R^1$ |
|---|---|---|
| 6a | Thiomorpholinyl | o-Cl-phenyl |
| 6b | N-methylpiperazinyl | o-Cl-phenyl |
| 6c | Thiomorpholinyl | o-F-phenyl |
| 6d | N-methylpiperazinyl | o-F-phenyl |
| 6e | Thiomorpholinyl | p-CH$_3$-phenyl |
| 6f | N-methylpiperazinyl | p-CH$_3$-phenyl |
| 6g | Thiomorpholinyl | o,p-Cl$_2$-phenyl |
| 6h | N-methylpiperazinyl | o,p-Cl$_2$-phenyl |
| 6i | Thiomorpholinyl | o,p-F$_2$-phenyl |
| 6j | N-methylpiperazinyl | o,p-F$_2$-phenyl |
| 6k | Thiomorpholinyl | 1-naphthyl |
| 6l | N-methylpiperazinyl | 1-naphthyl |

A preferred compound is N-(p-fluorophenyl)-2-methyl-3-thiomorpholinomethyl-5-(p-methylphenyl)pyrrole (6e).

Alternatively, the compound of the invention has the formula II, preferably with X=N; Y=CH; R=thiomorpholinyl or N-methylpiperazinyl; $R^2$=methyl; $R^1$=one of the residues $R^1$ present in compound 7a-l and displayed in Table 2.

TABLE 2

| Compd | R | $R^1$ |
|---|---|---|
| 7a | Thiomorpholinyl | o-Cl-phenyl |
| 7b | N-Methylpiperazinyl | o-Cl-phenyl |
| 7c | Thiomorpholinyl | o-F-phenyl |
| 7d | N-Methylpiperazinyl | o-F-phenyl |
| 7e | Thiomorpholinyl | p-CH$_3$-phenyl |
| 7f | N-Methylpiperazinyl | p-CH$_3$-phenyl |
| 7g | Thiomorpholinyl | o,p-Cl$_2$-phenyl |
| 7h | N-Methylpiperazinyl | o,p-Cl$_2$-phenyl |
| 7i | Thiomorpholinyl | o,p-F$_2$-phenyl |
| 7j | N-Methylpiperazinyl | o,p-F$_2$-phenyl |
| 7k | Thiomorpholinyl | 1-naphthyl |
| 7l | N-Methylpiperazinyl | 1-naphthyl |

A preferred compound is N-(o-fluorophenyl)-2-methyl-3-thiomorpholinomethyl-5-(p-fluorophenyl)pyrrole, 7c.

The compounds of the invention are suitable for therapeutic use, in particular for the preparation of antitubercular pharmaceutical compositions, particularly active at the early stage of the disease (latent phase), preferably in association with at least one compound having an antitubercular activity.

The invention also refers to the synthesis methods for the preparation of the compounds having the general formula I or II and to the synthetic intermediates of such methods.

The invention will now be described by means of non limiting examples.

Structure and Synthesis of Compounds 6a-l.

The procedure for the synthesis of compounds having structure 6a-l is the following:

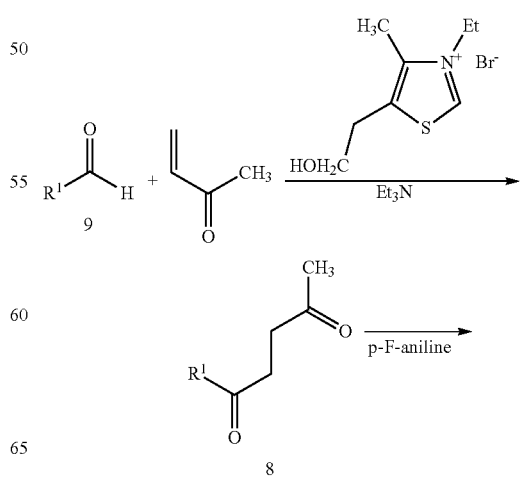

-continued

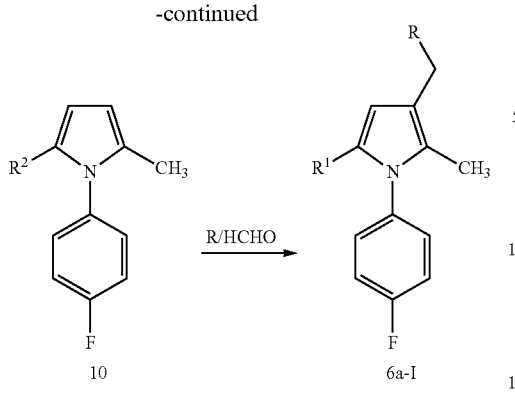

Preparation of Compounds Having Formula 8:

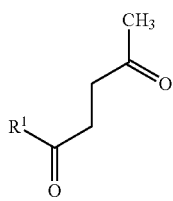

wherein $R^1$ is o-chlorophenyl, o-fluorophenyl, p-methylphenyl, o,p-dichlorophenyl, o,p-difluorophenyl, 1-naphthyl.

a) Methyl vinyl ketone (0.016 mol) was reacted with the appropriate aryl aldehyde (0.016 mol) having the following formula 9:

$$R^1\text{—CHO} \quad (9)$$

wherein
$R^1$ is o-chlorophenyl, o-fluorophenyl, p-methylphenyl, o,p-dichlorophenyl, o,p-difluorophenyl, 1-naphthyl;

in the presence of 3-ethyl-5-(2-hydroxyethyl)-4-methylthiazolium bromide (0.0032 mol) and triethylamine (0.011 mol);

b) the mixture was stirred at 75° C. under a nitrogen atmosphere for 5 h or 23 h, depending on the particular substrate;

c) after cooling, treat the mixture with aqueous HCl until pH 2.

d) keep the mixture under stirring for 30 min;

e) extract the mixture with ethyl acetate and neutralize the aqueous phase with a $NaHCO_3$ solution;

f) purify the product by column chromatography on aluminium oxide (Brockmann grade II-III), eluting with benzene.

Table 3 reports physico-chemical data of compounds 8.

TABLE 3

| Compd | $R^1$ | Mp, ° C. | Yield, % | Formula (MW) |
|---|---|---|---|---|
| 8a | 2-Cl-phenyl | 40 | 38 | $C_{11}H_{11}ClO_2$ (210.66) |
| 8b | 2-F-phenyl | 30 | 67 | $C_{11}H_{11}FO_2$ (194.2) |
| 8c | 4-$CH_3$-phenyl | 32 | 41 | $C_{12}H_{14}O_2$ (190.24) |
| 8d | 2,4-$Cl_2$-phenyl | 37 | 25 | $C_{11}H_{10}Cl_2O_2$ (245.1) |
| 8e | 2,4-$F_2$-phenyl | 41 | 20 | $C_{11}H_{10}F_2O_2$ (212.19) |
| 8f | 1-naphthyl | 35 | 28 | $C_{15}H_{14}O_2$ (226.27) |

2) Preparation of Compounds Having Formula 10:

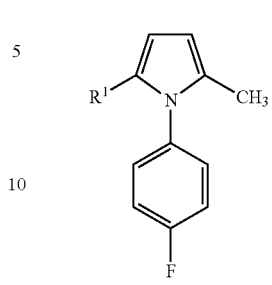

wherein
$R^1$ is o-chlorophenyl, o-fluorophenyl, p-methylphenyl, o,p-dichlorophenyl, o,p-difluorophenyl, 1-naphthyl a) the appropriate compound 8 was reacted with an equimolar amount of p-F-aniline;

b) the mixture was heated at 100° C. for 3 h;

c) the obtained products were purified by column chromatography on aluminium oxide (Brockmann grade II-III), eluting with cyclohexane.

Table 4 reports physico-chemical data of compounds 10.

TABLE 4

| Compd | $R^1$ | Mp, ° C. | Yield, % | Formula (MW) |
|---|---|---|---|---|
| 10a | 2-Cl-phenyl | 127 | 54 | $C_{17}H_{13}ClFN$ (285.74) |
| 10b | 2-F-phenyl | 125 | 84 | $C_{17}H_{13}F_2N$ (269.29) |
| 10c | 4-$CH_3$-phenyl | 132 | 75 | $C_{18}H_{16}FN$ (265.32) |
| 10d | 2,4-$Cl_2$-phenyl | 138 | 86 | $C_{17}H_{12}Cl_2FN$ (320.19) |
| 10e | 2,4-$F_2$-phenyl | 129 | 76 | $C_{17}H_{12}F_3N$ (287.28) |
| 10f | 1-naphthyl | 130 | 95 | $C_{21}H_{16}FN$ (301.36) |

3) Preparation of the Compounds Having General Formula 6a-l:

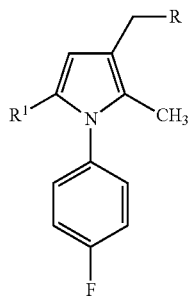

wherein
R is morpholinyl, thiomorpholinyl, N-methylpiperazinyl, N-isopropylpiperazinyl, N-acetylpiperazinyl, piperidyl or imidazolyl;

$R^1$ is o-chlorophenyl, o-fluorophenyl, p-methylphenyl, o,p-dichlorophenyl, o,p-difluorophenyl, 1-naphthyl a) allow to react 0.6 mol of a suitable amine (morpholine, thiomorpholine, N-methylpiperazine, N-acetylpiperazine, N-isopropylpiperazine, piperidine, imidazole) with 0.6 mol of 36.5% (w/w) aqueous formaldehyde using 5 mL of glacial acetic acid as solvent;

b) using a dropping funnel, add the appropriate compound 10 (0.6 mol), dissolved in 1:2 acetic acid/acetonitrile mixture, dropwise to the Mannich adduct;

c) stir the mixture for 12 h at 25° C.;

d) neutralize the mixture with 30 mL of 20% (w/v) aqueous NaOH;

e) extract the solution with ethyl acetate and wash the organic phase with water to neutrality;

f) purify the so obtained product by column chromatography on aluminium oxide (Brockmann grade II-III), eluting the derivatives containing the N-methylpiperazine moiety with chloroform and those containing the thiomorpholine moiety with benzene. Table 5 reports physico-chemical data of synthesized compounds 6a-l.

TABLE 5

| Compd | R | $R^1$ | Mp, °C. | Yield, % | Formula (MW) |
|---|---|---|---|---|---|
| 6a | Thiomorpholinyl | 2-Cl-phenyl | 95 | 83 | $C_{22}H_{22}ClFN_2S$ (400.94) |
| 6b | N-methyl-piperazinyl | 2-Cl-phenyl | 82 | 80 | $C_{23}H_{25}ClFN_3$ (397.92) |
| 6c | Thiomorpholinyl | 2-F-phenyl | 120 | 60 | $C_{22}H_{22}F_2N_2S$ (384.49) |
| 6d | N-methyl-piperazinyl | 2-F-phenyl | 83 | 40 | $C_{23}H_{25}F_2N_3$ (381.46) |
| 6e | Thiomorpholinyl | 4-$CH_3$-phenyl | Oil | 45 | $C_{23}H_{25}FN_2S$ (380.52) |
| 6f | N-methyl-piperazinyl | 4-$CH_3$-phenyl | 129 | 39 | $C_{24}H_{28}FN_3$ (377.50) |
| 6g | Thiomorpholinyl | 2,4-$Cl_2$-phenyl | 143 | 65 | $C_{22}H_{21}Cl_2FN_2S$ (435.39) |
| 6h | N-methyl-piperazinyl | 2,4-$Cl_2$-phenyl | 130 | 61 | $C_{23}H_{24}Cl_2FN_3$ (432.36) |
| 6i | Thiomorpholinyl | 2,4-$F_2$-phenyl | 100 | 63 | $C_{22}H_{21}F_3N_2S$ (402.48) |
| 6j | N-methyl-piperazinyl | 2,4-$F_2$-phenyl | 90 | 62 | $C_{23}H_{24}F_3N_3$ (399.45) |
| 6k | Thiomorpholinyl | 1-naphthyl | Oil | 72 | $C_{26}H_{25}FN_2S$ (416.55) |
| 6l | N-methyl-piperazinyl | 1-naphthyl | Oil | 38 | $C_{27}H_{28}FN_3$ (413.53) |

Melting points were determined with a Fisher-Jones apparatus and are uncorrected. Elemental analyses are within ±0.4% of theoretical values.

As an example, the preparation of compound 6e starting from 8c and 10c is reported:

1) Preparation of Compound 8c a) Methyl vinyl ketone (1.16 g, 0.016 mol) and p-tolualdehyde (2 g, 0.016 mol) were reacted in the presence of 3-ethyl-5-(2-hydroxyethyl)-4-methylthiazolium bromide (0.837 g, 0.0032 mol) and triethylamine (1.14 g, 0.011 mol).

b) Stir the reaction mixture at 75° C. under a nitrogen atmosphere for 24 h.

c) Cool the mixture to room temperature, add ice and 30 mL of concentrated HCl to the mixture until pH 2.

d) Stir for 30 min.

e) Extract with ethyl acetate and neutralize the combined organic fractions with an aqueous solution of $NaHCO_3$.

f) Dry the organic fraction on anhydrous sodium sulphate for 3 h.

g) Purify the product by column chromatography on aluminium oxide (Brockmann grade II-III), eluting with a 3:1 cyclohexane/ethyl acetate mixture (41% yield).

2) Preparation of Compound 10c a) Compound 8c (1.29 g, 0.007 mol) was reacted at 100° C. for 3 h with p-F-aniline (0.75 g, 0.007 mol) and p-toluenesulphonic acid (0.08 g).

b) Purify the obtained product by column chromatography on aluminium oxide (Brockmann grade II-III), eluting with cyclohexane (75% yield).

3) Preparation of Compound 6e a) Thiomorpholine (0.53 g, 0.0051 mol) and formaldehyde (0.153 g, 0.0051 mol, 36.5% w/w aqueous solution) were reacted using 5.5 mL of acetic acid as the solvent.

b) Through a dropping funnel, add the obtained Mannich adduct dropwise to a solution containing compound 10c (1.35 g, 0.0051 mol) in glacial acetic acid (11.8 mL) and acetonitrile (23.5 mL).

c) Stir the mixture for 12 h at 25° C.

d) Add 30 mL of 20% w/v aqueous NaOH to neutrality.

e) Extract the mixture with ethyl acetate and wash the extracts with water to neutrality.

f) Dry the organic phase on anhydrous sodium sulphate for 2 h.

g) Purify the product by column chromatography on aluminium oxide (Brockmann, grade II-III), eluting with benzene (yield 19.4%).

NMR Data for Compounds 6a-l

6a: $^1$H NMR ($CDCl_3$) δ: 2.07 (s, 3H, $CH_3$), 2.70 (m, thiomorpholine 4H), 2.80 (m, thiomorpholine 4H), 3.49 (s, 2H, $CH_2$), 6.28 (s, 1H, H-4), 6.92-7.36 (m, 8H, aromatic protons).

6b: $^1$H NMR ($CDCl_3$) δ: 2.08 (s, 3H, N—$CH_3$), 2.30 (s, 3H, $CH_3$), 2.49 (m, N-methylpiperazine 8H), 3.51 (s, 2H, $CH_2$), 6.31 (s, 1H, H-4), 6.28-7.27 (m, 8H, aromatic protons).

6c: $^1$H NMR ($CDCl_3$) δ: 2.08 (s, 3H, $CH_3$), 2.71 (m, thiomorpholine 4H), 2.78 (m, thiomorpholine 4H), 3.48 (s, 2H, $CH_2$), 6.34 (s, 1H, H-4), 6.87-7.36 (m, 8H, aromatic protons).

6d: $^1$H NMR ($CDCl_3$) δ: 2.08 (s, 3H, N—$CH_3$), 2.30 (s, 3H, $CH_3$), 2.49 (m, N-methylpiperazine 8H), 3.51 (s, 2H, $CH_2$), 6.36 (s, 1H, H-4), 6.94-7.26 (m, 8H, aromatic protons).

6e: $^1$H NMR ($CDCl_3$) δ: 2.05 (s, 3H, $CH_3$), 2.38 (s, 3H, $CH_3$), 2.71 (m, thiomorpholine 4H), 2.78 (m, thiomorpholine 4H), 3.46 (s, 2H, $CH_2$), 6.27 (s, 1H, H-4), 6.79-7.36 (m, 8H, aromatic protons).

6f: $^1$H NMR ($CDCl_3$) δ: 2.05 (s, 3H, N—$CH_3$), 2.30 (s, 3H, $CH_3$), 2.37 (s, 3H, $CH_3$), 2.38 (m, N-methylpiperazine 8H), 3.48 (s, 2H, $CH_2$), 6.30 (s, 1H, H-4), 6.79-7.30 (m, 8H, aromatic protons).

6g: $^1$H NMR ($CDCl_3$) δ: 2.08 (s, 3H, $CH_3$), 2.71 (m, thiomorpholine 4H), 2.77 (m, thiomorpholine 4H), 3.48 (s, 2H, $CH_2$), 6.28 (s, 1H, H-4), 6.96-7.36 (m, 7H, aromatic protons).

6h: $^1$H NMR ($CDCl_3$) δ: 2.09 (s, 3H, N—$CH_3$), 2.30 (s, 3H, $CH_3$), 2.54 (m, N-methylpiperazine 8H), 3.50 (s, 2H, $CH_2$), 6.31 (s, 1H, H-4), 6.98-7.29 (m, 7H, aromatic protons).

6i: $^1$H NMR ($CDCl_3$) δ: 2.06 (s, 3H, $CH_3$), 2.71 (m, thiomorpholine 4H), 2.78 (m, thiomorpholine 4H), 3.46 (s, 2H, $CH_2$), 6.29 (s, 1H, H-4), 6.66-7.36 (m, 7H, aromatic protons).

6j: $^1$H NMR ($CDCl_3$) δ: 2.07 (s, 3H, N—$CH_3$), 2.33 (s, 3H, $CH_3$), 2.49 (m, N-methylpiperazine 8H), 3.49 (s, 2H, $CH_2$), 6.31 (s, 1H, H-4), 6.65-7.27 (m, 7H, aromatic protons).

6k: $^1$H NMR ($CDCl_3$) δ: 2.14 (s, 3H, $CH_3$), 2.74 (m, thiomorpholine 4H), 2.85 (m, thiomorpholine 4H), 3.56 (s, 2H, $CH_2$), 6.32 (s, 1H, H-4), 6.83-8.03 (m, 11H, aromatic protons).

6l: $^1$H NMR ($CDCl_3$) δ: 2.14 (s, 3H, N—$CH_3$), 2.32 (s, 3H, $CH_3$), 2.47 (m, N-methylpiperazine 8H), 3.60 (s, 2H, $CH_2$), 6.34 (s, 1H, H-4), 6.80-8.01 (m, 11H, aromatic protons).

The NMR spectra were recorded with a Brucker 400 (MHz) spectrometer employing deuterochloroform ($CDCl_3$) as the solvent. Tetramethylsilane (TMS) was used as an internal standard.

Structure and Synthesis of Compounds 7a-l.

The following synthetic scheme was adopted for the synthesis of compounds having structure 7a-l.

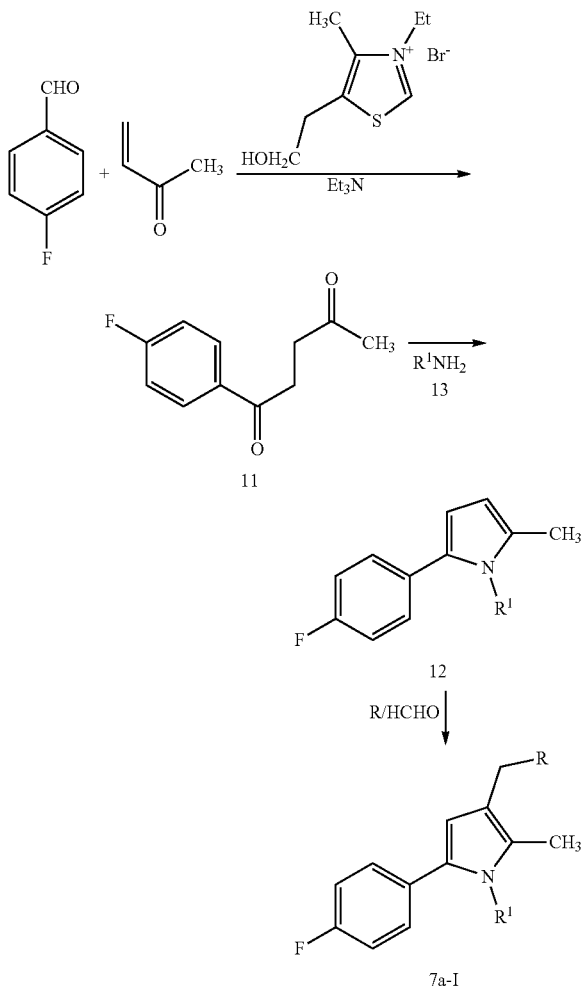

1) Preparation of Compounds Having Formula 11:

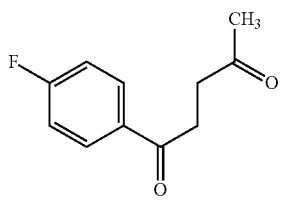

a) allow to react methyl vinyl ketone (0.016 mol), p-F-benzaldehyde (0.016 mol), 3-ethyl-5-(2-hydroxyethyl)-4-methylthiazolium bromide (0.0032 mol) and triethylamine (0.011 mol);
b) stir the mixture at 75° C. under a nitrogen atmosphere for 5 h or for 23 h, depending on the substrate;
c) cool the mixture and treat it with aqueous HCl until pH 2;
d) stir the mixture for 30 min;
e) extract the mixture with ethyl acetate and neutralize the extracts washing with aqueous $NaHCO_3$;
f) purify the product by column chromatography on aluminium oxide (Brockmann, grade II-III), using benzene as eluant.

2) Preparation of Compounds Having Formula 12:

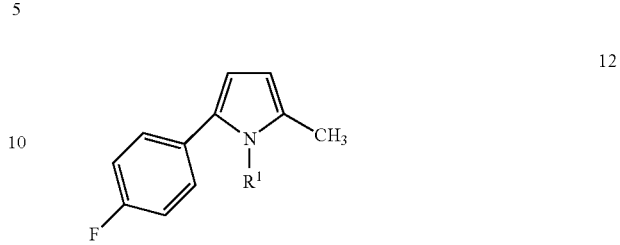

wherein
$R^1$ is o-chlorophenyl, o-fluorophenyl, p-methylphenyl, o,p-dichlorophenyl, o,p-difluorophenyl, 1-naphthyl
a) make compound 11 to react with an equimolar amount of the suitable aromatic amine having the general formula 13;

$$R^1-NH_2 \qquad (13)$$

wherein
$R^1$ is o-chlorophenyl, o-fluorophenyl, p-methylphenyl, o,p-dichlorophenyl, o,p-difluorophenyl, 1-naphthyl.
b) allow the mixture to react at 100° C. for 3 h;
c) purify the obtained products by column chromatography on aluminium oxide, eluting with cyclohexane.

Table 6 reports physico-chemical data for compounds 12.

TABLE 6

| Compd | $R^1$ | Mp, ° C. | Formula (MW) |
|---|---|---|---|
| 12a | 2-Cl-phenyl | 72 | $C_{17}H_{13}ClFN$ (285.74) |
| 12b | 2-F-phenyl | 83 | $C_{17}H_{13}F_2N$ (269.29) |
| 12c | 4-$CH_3$-phenyl | 80 | $C_{18}H_{16}FN$ (265.32) |
| 12d | 2,4-$Cl_2$-phenyl | 67 | $C_{17}H_{12}Cl_2FN$ (320.19) |
| 12e | 2,4-$F_2$-phenyl | 85 | $C_{17}H_{12}F_3N$ (287.28) |
| 12f | 1-naphthyl | 80 | $C_{21}H_{16}FN$ (301.36) |

3) Preparation of Compounds Having General Formula 7a-l:

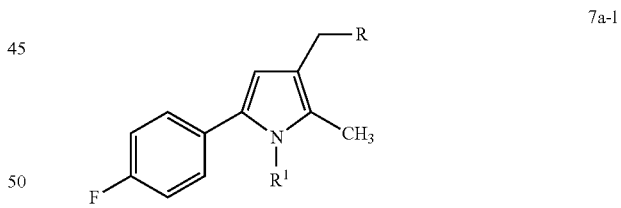

wherein
R is morpholinyl, thiomorpholinyl, N-methylpiperazinyl, N-isopropylpiperazinyl, N-acetylpiperazinyl, piperidyl or imidazolyl;
$R^1$ is o-chlorophenyl, o-fluorophenyl, p-methylphenyl, o,p-dichlorophenyl, o,p-difluorophenyl, 1-naphthyl.
a) react 0.6 mol of a suitable base (morpholine, thiomorpholine, N-methylpiperazine, N-acetylpiperazine, N-isopropylpiperazine, piperidine, imidazole) with 0.6 mol of 36.5% w/w aqueous formaldehyde employing 5 mL of glacial acetic acid as solvent;
b) through a dropping funnel, add the formed Mannich adduct dropwise to a solution of the appropriate compound 12 (0.6 mol) in a 1:2 acetic acid/acetonitrile mixture;
c) stir the mixture for 12 h at 25° C.;

d) neutralize the mixture with 30 mL of 20% w/v aqueous NaOH;

e) extract the solution with ethyl acetate and wash the organic phase with water to neutrality;

f) purify the obtained product by column chromatography on aluminium oxide (Brockmann, grade II-III), eluting the derivatives containing the N-methylpiperazine moiety with chloroform and the derivatives containing the thiomorpholine one with benzene.

In Table 7, physico-chemical data for some of the compounds 7a-l are reported.

TABLE 7

| Compd | R | $R^1$ | Mp, °C. | Yield, % | Formula (MW) |
|---|---|---|---|---|---|
| 7a | Thiomorpholinyl | 2-Cl-phenyl | Oil | 30 | $C_{22}H_{22}ClFN_2S$ (400.94) |
| 7b | N-Methyl-piperazinyl | 2-Cl-phenyl | Oil | 41 | $C_{23}H_{25}ClFN_3$ (397.92) |
| 7c | Thiomorpholinyl | 2-F-phenyl | Oil | 35 | $C_{22}H_{22}F_2N_2S$ (384.49) |
| 7d | N-Methyl-piperazinyl | 2-F-phenyl | Oil | 37 | $C_{23}H_{25}F_2N_3$ (381.46) |
| 7e | Thiomorpholinyl | 4-$CH_3$-phenyl | 132 | 36 | $C_{23}H_{25}FN_2S$ (380.52) |
| 7f | N-Methyl-piperazinyl | 4-$CH_3$-phenyl | 132 | 50 | $C_{24}H_{28}FN_3$ (377.50) |
| 7g | Thiomorpholinyl | 2,4-$Cl_2$-phenyl | 110 | 56 | $C_{22}H_{21}Cl_2FN_2S$ (435.39) |
| 7h | N-Methyl-piperazinyl | 2,4-$Cl_2$-phenyl | Oil | 52 | $C_{23}H_{24}Cl_2FN_3$ (432.36) |
| 7i | Thiomorpholinyl | 2,4-$F_2$-phenyl | Oil | 50 | $C_{22}H_{21}F_3N_2S$ (402.48) |
| 7j | N-Methyl-piperazinyl | 2,4-$F_2$-phenyl | 105 | 40 | $C_{23}H_{24}F_3N_3$ (399.45) |
| 7k | Thiomorpholinyl | 1-naphthyl | 130 | 26 | $C_{26}H_{25}FN_2S$ (416.55) |
| 7l | N-Methyl-piperazinyl | 1-naphthyl | 125 | 64 | $C_{27}H_{28}FN_3$ (413.53) |

Melting points were determined with a Fisher-Jones apparatus and are uncorrected. All synthesized derivatives have been subjected to elemental analysis. Elemental analyses are within ±0.4% of theoretical values.

Hereafter, the preparation of compound 7c starting from 12b is described.

Preparation of Compound 12b a) Compound 11 (1.25 g, 0.006 mol) was reacted with o-F-aniline (0.71 g, 0.006 mol) and p-toluenesulphonic acid (0.08 g);

b) Allow the reaction to proceed at 100° C. for 5 h;

c) Purify the obtained product by column chromatography on aluminium oxide (activity grade II-III, according to Brockmann), eluting with cyclohexane (yield 82%).

Preparation of Compound 7c a) Thiomorpholine (0.53 g, 0.0051 mol) was reacted with formaldehyde (0.153 g, 0.0051 mol, 36.5% w/w aqueous solution) using 5.5 mL of acetic acid as solvent.

b) Through a dropping funnel, add the Mannich adduct dropwise to a solution containing compound 12b (1.4 g, 0.0053 mol) in glacial acetic acid (12.2 mL) and acetonitrile (24.4 mL).

c) Stir the reaction for 12 h at 25° C.

d) Neutralize with 30 mL of a 20% w/v aqueous solution of NaOH.

e) Extract the mixture with ethyl acetate and wash the organic extracts with water to neutrality.

f) Dry the organic extracts on anhydrous sodium sulphate for 2 h.

g) Purify the product by column chromatography on silica gel eluting with ethyl acetate (yield 23%).

NMR Data for Compounds 7a-l

7a: $^1$H NMR (CDCl$_3$) δ: 1.97 (s, 3H, CH$_3$), 2.72 (m, thiomorpholine 4H), 2.78 (m, thiomorpholine 4H), 3.48 (s, 2H, CH$_2$), 6.31 (s, 1H, H-4), 6.79-7.48 (m, 8H, aromatic protons).

7b: $^1$H NMR (CDCl$_3$) δ: 1.94 (s, 3H, N—CH$_3$), 2.30 (s, 3H, CH$_3$), 2.33 (m, N-methylpiperazine 8H), 3.50 (s, 2H, CH$_2$), 6.34 (s, 1H, H-4), 6.36-7.48 (m, 8H, aromatic protons).

7c: $^1$H NMR (CDCl$_3$) δ: 2.03 (s, 3H, CH$_3$), 2.71 (m, thiomorpholine 4H), 2.77 (m, thiomorpholine 4H), 3.47 (s, 2H, CH$_2$), 6.29 (s, 1H, H-4), 6.80-733 (m, 8H, aromatic protons).

7d: $^1$H NMR (CDCl$_3$) δ: 2.04 (s, 3H, N—CH$_3$), 2.35 (s, 3H, CH$_3$), 2.55 (m, N-methylpiperazine 8H), 3.55 (s, 2H, CH$_2$), 6.34 (s, 1H, H-4), 6.83-7.34 (m, 8H, aromatic protons).

7e: $^1$H NMR (CDCl$_3$) δ: 2.05 (s, 3H, CH$_3$), 2.25 (s, 3H, CH$_3$), 2.72 (m, thiomorpholine 4H), 2.80 (m, thiomorpholine 4H), 3.48 (s, 2H, CH$_2$), 6.29 (s, 1H, H-4), 6.92-7.12 (m, 8H, aromatic protons).

7f: $^1$H NMR (CDCl$_3$) δ: 2.05 (s, 3H, N—CH$_3$), 2.30 (s, 3H, CH$_3$), 2.37 (s, 3H, CH$_3$), 2.50 (m, N-methylpiperazine 8H), 3.48 (s, 2H, CH$_2$), 6.30 (s, 1H, H-4), 6.79-7.30 (m, 8H, aromatic protons).

7g: $^1$H NMR (CDCl$_3$) δ: 1.97 (s, 3H, CH$_3$), 2.70 (m, thiomorpholine 4H), 2.76 (m, thiomorpholine 4H), 3.47 (s, 2H, CH$_2$), 6.30 (s, 1H, H-4), 6.86-7.49 (m, 7H, aromatic protons).

7h: $^1$H NMR (CDCl$_3$) δ: 1.97 (s, 3H, N—CH$_3$), 2.27 (s, 3H, CH$_3$), 2.48 (m, N-methylpiperazine 8H), 3.43 (s, 2H, CH$_2$), 6.32 (s, 1H, H-4), 6.82-7.48 (m, 7H, aromatic protons).

7i: $^1$H NMR (CDCl$_3$) δ: 2.04 (s, 3H, CH$_3$), 2.71 (m, thiomorpholine 4H), 2.77 (m, thiomorpholine 4H), 3.46 (s, 2H, CH$_2$), 6.29 (s, 1H, H-4), 6.84-7.26 (m, 7H, aromatic protons).

7j: $^1$H NMR (CDCl$_3$) δ: 2.05 (s, 3H, N—CH$_3$), 2.29 (s, 3H, CH$_3$), 2.50 (m, N-methylpiperazine 8H), 3.50 (s, 2H, CH$_2$), 6.32 (s, 1H, H-4), 6.79-7.37 (m, 7H, aromatic protons).

7k: $^1$H NMR (CDCl$_3$) δ: 1.87 (s, 3H, CH$_3$), 2.76 (m, thiomorpholine 4H), 2.83 (m, thiomorpholine 4H), 3.54 (s, 2H, CH$_2$), 6.41 (s, 1H, H-4), 6.64-7.89 (m, 11H, aromatic protons).

7l: $^1$H NMR (CDCl$_3$) δ: 1.90 (s, 3H, N—CH$_3$), 2.32 (s, 3H, CH$_3$), 2.53 (m, N-methylpiperazine 8H), 3.56 (s, 2H, CH$_2$), 6.44 (s, 1H, H-4), 6.63-7.90 (m, 11H, aromatic protons).

The NMR spectra were recorded with a Brucker 400 (MHz) spectrometer employing deuterochloroform (CDCl$_3$) as solvent. Tetramethylsilane (TMS) was used as an internal standard.

Microbiological Activity

Compounds 6a-l and 7a-l were tested in DMSO.

a) Antimycobacterial Activity

Compounds 6a-l and 7a-l were preliminarily assayed against two freshly isolated clinical strains, *M. fortuitum* CA10 and *M. tuberculosis* B814, according to the dilution method in agar (Hawkins et al., 1991)

Growth media were Mueller-Hinton (Difco) containing 10% of OADC (oleic acid, albumine and dextrose complex) for *M. fortuitum* and Middlebrook 7H11 agar (Difco) with 10% of OADC (albumine and dextrose complex) for *M. tuberculosis*. Substances were tested at the single dose of 100 mg/mL. The active compounds were then assayed for inhibitory activity against a variety of mycobacterium strains in Middlebrok 7H9 broth using the NCCLS procedure. The mycobacterium species used for biological tests were *M. tuberculosis* 103471 and, among atypical mycobacteria, *M. smegmatis* 103599, *M. marinum* 6423 and *M. avium* 103317 (from the Institute Pasteur collection).

In all cases, minimum inhibitory concentrations (MICs in μg/mL) for each compound were determined. The MIC was defined as the lowest concentration of drug that yielded an absence of visual turbidity. Stock solutions of substances were prepared by dissolving a known weight of the compound in DMSO. The stock solutions were sterilized by passage through a 0.2 μm Nylon membrane filter. Serial 2-fold dilutions of the compounds with water were prepared. The tubes were incubated at 37° C. for 3-21 days. A control tube without any compound was included in each experiment. BM212, Isoniazid (INH), streptomycin and rifampin were used as reference compounds.

Inhibitory Activity of 6e and 7c on Intramacrophagic Mycobacteria.

The bactericidal activity of such compounds on intracellular mycobacteria was studied on U937 cells (INC-FLOW), a human hystiocytic cell line. Cells were differentiated into macrophages with 20 ng/mL of phorbol myristate acetate (PMA, Sigma) and grown in RPMI 1640 medium with 10% fetal calf serum.

Inhibitory activity of 6e and 7c on multidrug-resistant mycobacteria A panel of twelve mycobacteria resistant to currently available antitubercular drugs, were used. Compounds 6e and 7c were tested on multiresistant *M. tuberculosis* strains in Middlebrook 7119 broth enriched with 10% ADC (Difco) using the macrodilution broth method.

b) Cytotoxic Activity Assays

The cytotoxicity was evaluated on Vero cell monolayers (ICN-Flow). They were inoculated in 6-well plates each containing $9 \times 10^4$ cells and incubated in DMEM with 5% FCS for 24 h at 37° C. in a 5% $CO_2$ incubator. After 24 h of culture, the medium was changed and a new medium containing decreasing doses of the substances under study was added.

After 5 days, the cells were trypsinized and counted in a Neubauer chamber under a light microscope. All the tests were done in triplicate. The maximum 50% non-toxic dose ($MNTD_{50}$) was defined as the drug concentration that decreased cell multiplication less than 50% with respect to the control.

c) Protection Index

Protection Index (PI), is the $MNTD_{50}/MIC$ ratio.

Results

The microbiological results relative to the tests against extracellular *M. tuberculosis* and atypical Mycobacteria are reported in Tables 8-13, as well as the PI, the cytotoxicity, and the activity against intracellular *M. tuberculosis* and multi drug resistant strains (MDR-TB). The inhibitory activity toward extracellular *M. tuberculosis* accounts for the ability of tested compounds to treat active tuberculosis. Differently, assays on intracellular *M. tuberculosis* assess the ability of tested compounds to inhibit mycobacteria during the latent phase of tuberculosis, before latent tuberculosis infection itself progresses to active disease.

TABLE 8

Cytotoxicity, antimycobacterial activity toward *M. tuberculosis* and protection index of compounds 6a-l.

| Compd | $MNTD_{50}$ (μg/mL) VERO cells | *M. tuberculosis* 103471 MIC (μg/mL) | Protection Index (PI) |
|---|---|---|---|
| BM212 | 4 | 0.70 | 5.7 |
| 6a | 4 | 4 | 1 |
| 6b | 2 | 8 | 0.25 |
| 6c | 16 | 0.5 | 32 |
| 6d | 4 | 16 | 0.25 |
| 6e | 64 | 0.4 | 160 |
| 6f | 8 | 4 | 2 |
| 6g | 64 | 2 | 32 |
| 6h | 16 | 8 | 2 |
| 6i | 16 | 0.5 | 32 |
| 6j | 8 | 4 | 2 |
| 6k | >128 | >16 | — |
| 6l | 4 | 16 | — |
| Isoniazid | 32 | 0.25 | 128 |
| Streptomycin | >64 | 0.50 | 128 |
| Rifampin | 64 | 0.3 | 213 |

TABLE 9

Antimycobacterial activity of compounds 6a-l toward atypical mycobacteria.

| | MIC (μg/mL) | | |
|---|---|---|---|
| Compd | *M. smegmatis* 103599 | *M. marinum* 6423 | *M. avium* 103317 |
| BM212 | 25 | 100 | 0.4 |
| 6a | >16 | >16 | 16 |
| 6b | >16 | >16 | 16 |
| 6c | >16 | >16 | 16 |
| 6d | >16 | >16 | >16 |
| 6e | 16 | 8 | 8 |
| 6f | 8 | >16 | 4 |
| 6g | >16 | >16 | 4 |
| 6h | >16 | >16 | 2 |
| 6i | >16 | 16 | 16 |
| 6j | >16 | >16 | 16 |
| 6k | >16 | >16 | >16 |
| 6l | >16 | 16 | 8 |
| Isoniazid | 64 | 16 | 32 |
| Streptomycin | 8 | 32 | 8 |
| Rifampin | 32 | 0.6 | 0.3 |

TABLE 10

Cytotoxicity, antimycobacterial activity toward *M. tuberculosis* and protection index of compounds 7a-l.

| Comp | $MNTD_{50}$ (μg/mL) VERO cells | *M. tuberculosis* 103471 MIC (μg/mL) | Protection Index (PI) |
|---|---|---|---|
| BM212 | 4 | 0.70 | 5.6 |
| 7a | 8 | 2 | 4 |
| 7b | 8 | 4 | 2 |
| 7c | 8 | 0.5 | 16 |
| 7d | 8 | 8 | 1 |
| 7e | 8 | 4 | 2 |
| 7f | 8 | 16 | 0.5 |
| 7g | 4 | 1 | 4 |
| 7h | 2 | 4 | 0.5 |
| 7i | 16 | 2 | 8 |
| 7j | 16 | 16 | 1 |
| 7k | 2 | 4 | 0.5 |
| 7l | 4 | 4 | 1 |
| Isoniazid | 32 | 0.25 | 128 |
| Streptomycin | >64 | 0.50 | 128 |
| Rifampin | 64 | 0.3 | 213 |

TABLE 11

Antimycobacterial activity of compounds
7a-l toward atypical mycobacteria.

| | MIC (µg/mL) | | |
|---|---|---|---|
| Compd | M. smegmatis 103599 | M. marinum 6423 | M. avium 103317 |
| BM212 | 25 | 100 | 0.4 |
| 7a | >16 | >16 | >16 |
| 7b | >16 | >16 | >16 |
| 7c | 8 | >16 | 8 |
| 7d | 0.3 | >16 | 16 |
| 7e | 16 | 8 | 8 |
| 7f | >16 | 8 | 16 |
| 7g | 16 | 8 | 2 |
| 7h | >16 | 8 | 4 |
| 7i | >16 | 16 | 16 |
| 7j | >16 | 16 | 16 |
| 7k | >16 | 16 | 8 |
| 7l | >16 | 8 | 8 |
| Isoniazid | 64 | 16 | 32 |
| Streptomycin | 8 | 32 | 8 |
| Rifampin | 32 | 0.6 | 0.3 |

TABLE 12

Activity of compounds 6e and 7c against
intracellular M. tuberculosis.

| Compound | MIC (µg/mL) Inhibition of intramacrophagic mycobacteria |
|---|---|
| 6e | 3 |
| 7c | 3 |
| Rifampin | 3 |

TABLE 13

Activity toward multi drug resistant strains (MDR-TB).

| Strain | SM 1 µg/mL | INH 0.1 µg/mL | RIF 1 µg/mL | EMB 5 µg/mL | 7c MIC (µg/mL) | 6e MIC (µg/mL) |
|---|---|---|---|---|---|---|
| 149/03 | S | R | R | S | 2 | 0.5 |
| 421/96 | S | S | R | S | 2 | 0.5 |
| 586/98 | S | S | R | S | 2 | 0.5 |
| 43/05 | S | S | S | S | 0.5 | 0.5 |
| 158/97 | S | S | S | R | 0.5 | 0.5 |
| 134/02 | R | R | S | S | 2 | 0.5 |
| 520/98 | R | S | R | S | 2 | 0.5 |
| 326/04 | R | R | S | R | >32 | 32 |
| 296/04 | S | S | R | R | 2 | 0.5 |
| 482/98 | S | S | R | S | 2 | 0.5 |
| 275/05 | R | S | S | S | 2 | 0.5 |
| H37Rv | S | S | S | S | 2 | 0.5 |

The compounds can be usefully employed in medical care. For example, compounds 6e and 7c are characterized by a very interesting biological profile. In particular, their activity against M. tuberculosis 103471 (0.4 µg/mL for 6e and 0.5 µg/mL for 7c, Table 8 and Table 10, respectively) is comparable to that shown by isoniazid (0.25 µg/mL), streptomycin (0.50 µg/mL) and rifampin (0.30 µg/mL), as well as to that of the parent compound BM212 (0.70 µg/mL). In addition, compounds 6e and 7c have the advantage to be less toxic, and particularly 6e is endowed with a very good protection index (PI=160), which is better than that found for isoniazid and streptomycin (PI=128) and slightly lower than that found for rifampin (PI=213). Moreover, compounds 6c, 6i, and 7g also showed good antimycobacterial activity (0.5, 0, 0.5, and 1 µg/mL, respectively).

In general, tested compounds showed activity toward atypical mycobacteria at concentrations higher than 8 µg/mL (Tables 9 and 11), suggesting a significant selectivity toward M. tuberculosis with respect to atypical mycobacteria. Significant exceptions were represented by activity toward M. avium, found to be in the range between 2 and 4 µg/mL for compounds 6f-h and 7g-h. Finally, 7d showed a 0.3 µg/mL activity toward M. smegmatis.

Compounds 6e and 7c, showing the best activity toward M. tuberculosis, were also tested against intracellular and resistant mycobacteria. Biological results reported in Table 12 showed that both of them exerted bactericidal activity on intracellular mycobacteria at 3 µg/mL concentration, comparable to that of rifampin. This result was very important because mycobacteria can reside for years inside lymphoid cells and macrophages (latent tuberculosis) and many traditional drugs were unable to get throw it. Moreover, combating latent tuberculosis infection is one of the major challenges mainly for reducing the high rate of progression to active disease in immuno-compromised individuals.

Finally, Table 13 showed that all of the tested strains were inhibited by compounds 6e and 7c at concentrations ranging from 0.5 to 2 µg/mL. The sole exception was represented by the 326/04 strain, sensitive to such compounds at concentrations higher than 32 µg/mL.

The present experimental evidences make these compounds extremely interesting when compared to the compounds now used in therapy, which tend to be less active against drug-resistant mycobacteria. As a consequence, toward drug-resistant mycobacteria a multi-drug therapy is needed today. In this context, considering the reduced toxicity of the pyrrole derivatives reported here, they could be usefully employed, alone or in combination, for the therapy of tuberculosis.

BIBLIOGRAPHY

Duncan, K. et al. Curr. Opin. Microbiol. 7, 460-465, 2004

Deidda, D. et al, Antimicrob. Agents Chemother. 42, 3035-3037, 1998

Biava M., et al Bioorg. Med. Chem. Lett. 9, 2983-2988, 1999

Biava M., et al Med. Chem. Res. 9, 19-34, 1999b

Biava M., et al Bioorg. Med. Chem. 11, 515-520, 2003

Biava M., et al Bioorg. Med. Chem. 12, 1453-1458, 2004

Biava M., et al Bioorg. Med. Chem. 13, 1221-1230, 2005

Hawkins, J. E.; Wallace Jr., R. J.; Brown, A.; 1991, Antibacterial susceptibility test: Mycobacteria: in A. Balows, W. J. Hausler Jr., K. L. Hermann, H. D. Isenberg, H. J. Shadomy (eds.). Manual of Clinical Microbiology, 5th edn., American Society for Microbiology, Washington, D.C.

The invention claimed is:

1. Compounds having general formula I:

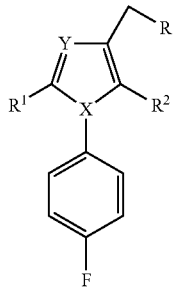

wherein
X is N;
Y is CH;
R is morpholinyl,
R₁ is p-methylphenyl, p-ethylphenyl, p-propylphenyl, p-isopropylphenyl, p-methoxyphenyl, o-fluorophenyl; and
R₂ is methyl.

2. A compound of claim 1 being N-(4-fluorophenyl)-2-methyl-3-morpholinyl-5-(4-methylphenyl)pyrrole.

3. A compound of claim 1 being N-(4-fluorophenyl)-2-methyl-3-morpholinyl-5-(4-ethylphenyl)pyrrole.

4. A compound of claim 1 being N-(4-fluorophenyl)-2-methyl-3-morpholinyl-5-(4-propylphenyl)pyrrole.

5. A compound of claim 1 being N-(4-fluorophenyl)-2-methyl-3-morpholinyl-5-(4-isopropylphenyl)pyrrole.

6. A compound of claim 1 being N-(4-fluorophenyl)-2-methyl-3-morpholinyl-5-(4-methoxyphenyl)pyrrole.

7. A compound of claim 1 being N-(4-fluorophenyl)-2-methyl-3-morpholinyl-5-(2-fluorophenyl)pyrrole.

8. A method for the preparation of a pharmaceutical composition for treating tuberculosis comprising admixing an effective non-toxic amount of a compound of claim 1 with a pharmaceutically acceptable carrier.

9. The method of claim 8, wherein the pharmaceutical composition comprises a second active compound for treatment of tuberculosis.

10. A pharmaceutical composition comprising a compound of claim 1 and excipients and diluents.

11. The pharmaceutical composition of claim 10 further comprising a second compound endowed with antitubercular activity.

12. Compounds having general formula II

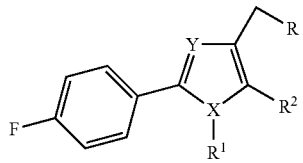

wherein
X is N;
Y is CH;
R is morpholinyl;
R₁ is o-fluorophenyl, p-methylphenyl, p-ethylphenyl, p-propylphenyl, p-isopropylphenyl, p-methoxyphenyl;
R₂ is methyl.

13. A compound of claim 12 being N-(2-fluorophenyl)-2-methyl-3-morpholinyl-5-(4-fluorophenyl)pyrrole.

14. A compound of claim 12 being N-(4-methylphenyl)-2-methyl-3-morpholinyl-5-(–4-fluorophenyl)pyrrole.

15. A compound of claim 12 being N-(4-ethylphenyl)-2-methyl-3-morpholinyl-5-(4-fluorophenyl)pyrrole.

16. A compound of claim 12 being N-(4-propylphenyl)-2-methyl-3-morpholinyl-5-(4-fluorophenyl)pyrrole.

17. A compound of claim 12 being N-(4-isopropyphenyl)-2-methyl-3-morpholinyl-5-(4-fluorophenyl)pyrrole.

18. A compound of claim 12 being N-(4-methoxyphenyl)-2-methyl-3-morpholinyl-5-(4-fluorophenyl)pyrrole.

19. A method for the preparation of a pharmaceutical composition for treatment of tuberculosis, comprising admixing an effective, non toxic amount of a compound of claim 11 with a pharmaceutical acceptable carrier.

20. The method of claim 19, wherein the pharmaceutical composition comprises a second active compound for treatment of tuberculosis.

21. A pharmaceutical composition comprising a compound according to claim 11 and excipients and diluents.

22. The pharmaceutical composition of claim 21, further comprising a second compound endowed with antitubercular activity.

* * * * *

UNITED STATES PATENT AND TRADEMARK OFFICE
CERTIFICATE OF CORRECTION

PATENT NO. : 8,012,970 B2
APPLICATION NO. : 13/033117
DATED : September 6, 2011
INVENTOR(S) : Mariangela Biava et al.

It is certified that error appears in the above-identified patent and that said Letters Patent is hereby corrected as shown below:

Items (75) and (73) on the cover page of the patent should be deleted and item (76) should be instead inserted and read,
-- (76) Inventors: Mariangela Biava, Rome (IT); Fabrizio Manetti, Castelnuovo Berardenga (IT); Delia Deidda, Siena (IT); Raffaello Pompei, Cagliari (IT); Maurizio Botta, Castelnuovo Berardenga (IT); Giulio Cesare Porretta, Rome (IT). --.

Item (63) on the cover page of the patent should read,
(63) Continuation of application No. 11/817,678, filed on Jun. 24, 2009, now Pat. No. 7,910,581, which is a 371 of application No. PCT/IT2006/000131, filed on Mar. 3, 2006.

In column 5, lines 30 - 31, the chemical formula "X═N and Y═N or CH;" should appear as follows:
-- X = N and Y = N or CH; --.

In column 5, lines 32 - 33, the chemical formula "X═O, S or N and Y═N or CH" should appear as follows: -- X = O, S or N and Y = N or CH --.

In column 5, line 34, the chemical formula "X═O, or S, R1" should appear as follows:
-- X = O, or S, R1 --.

In column 5, line 36, the chemical formula "X═N, Y═CH, R═N-methylpiperazinyl" should appear as follows: -- X = N, Y = CH, R = N-methylpiperazinyl --.

In column 5, line 37, the chemical formula "R2═CH3" should appear as follows: -- R2 = CH3 --.

In column 5, line 40, the chemical formula "X═N, Y═CH, R═N-methylpiperazinyl" should appear as follows: -- X = N, Y = CH, R = N-methylpiperazinyl --.

Signed and Sealed this
Twenty-fifth Day of September, 2012

David J. Kappos
*Director of the United States Patent and Trademark Office*

In column 5, line 41, the chemical formula "R2═CH3" should appear as follows:
-- R2 = CH3 --.

In column 5, line 44, the chemical formula "X═O, Y═CH," should appear as follows:
-- X = O, Y = CH, --.

In column 5, line 45, the chemical formula "R2═CH3" should appear as follows: -- R2 = CH3 --.

In column 5, line 47, the chemical formula "X═N; Y═CH;" should appear as follows:
-- X = N; Y = CH; --.

In column 6, line 4, the chemical formula "X═N; Y═CH;" should appear as follows:
-- X = N; Y = CH; --.